United States Patent [19]
Blewett et al.

[11] Patent Number: 6,106,521
[45] Date of Patent: *Aug. 22, 2000

[54] APPARATUS FOR THERMAL TREATMENT OF TISSUE

[75] Inventors: Jeffrey J. Blewett, Plantsville; Christopher W. Maurer, Newtown, both of Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/689,958

[22] Filed: Aug. 16, 1996

[51] Int. Cl.[7] ................................................ A61B 18/18

[52] U.S. Cl. ............................ 606/41; 607/101; 600/105

[58] Field of Search ............................... 607/96, 98–102, 607/113, 115, 116; 606/34, 37–42, 45–50; 604/19–22; 600/104, 105

[56] References Cited

U.S. PATENT DOCUMENTS

| Re. 32,057 | 12/1985 | LeVeen . |
|---|---|---|
| Re. 32,066 | 1/1986 | Leveen . |
| 3,991,770 | 11/1976 | LeVeen . |

(List continued on next page.)

FOREIGN PATENT DOCUMENTS

| 0608609 | 8/1994 | European Pat. Off. . |
|---|---|---|
| 2941060 | 4/1980 | Germany . |
| 3247793 | 7/1983 | Germany . |
| 2121675 | 5/1990 | Japan . |
| 2119253 | 11/1983 | United Kingdom . |
| 9004365 | 5/1990 | WIPO . |
| 9103996 | 4/1991 | WIPO . |
| 9116859 | 11/1991 | WIPO . |
| 9210142 | 6/1992 | WIPO . |
| 9220290 | 11/1992 | WIPO . |
| 9304727 | 3/1993 | WIPO . |
| 9315664 | 8/1993 | WIPO . |
| 9513027 | 5/1995 | WIPO . |
| WO 96 10367 | 4/1996 | WIPO . |
| WO 96 34571 | 11/1996 | WIPO . |
| 9706857 | 2/1997 | WIPO . |

OTHER PUBLICATIONS

Olinger et al., "Eighteen–Gauge Microscopic–Telescopic Needle Endoscope with Eletrode Channel: Potential Clinical and Research Application", *Surgical Neurology*, May 1974, pp. 151–159.

RADIONICS® Neurosurgical Instruments, 1981 Radionics, Inc.

*Primary Examiner*—Linda C. M. Dvorak
*Assistant Examiner*—Bryan K. Yarnell

[57] ABSTRACT

An apparatus for the radio-frequency (RF) thermal treatment of tissue, particularly, prostatic tissue is intended for use in conjunction with a conventional endoscope. The apparatus includes an elongate member having at least one passageway extending at least partially along its length, a delivery tube disposed within the passageway and having a memory portion comprised of a shape memory material, and being moveable within the passageway to extend the memory portion from the elongate member to permit the memory portion to assume a normal unstressed curved configuration, an electromagnetic probe disposed within the delivery tube and moveable within the delivery tube to extend a probe end portion beyond the delivery tube and within tissue. The electromagnetic probe has sufficient flexibility to follow the curved path defined by the memory portion of the delivery tube. The elongate member of the apparatus may further include a channel dimensioned to receive a conventional endoscope. Proximally positioned actuators permit selective movement of the delivery tube and electromagnetic probe. A system for thermal treatment of tissue includes a thermal treatment apparatus and an endoscope which is positioned within a working channel of the apparatus.

17 Claims, 7 Drawing Sheets

U.S. PATENT DOCUMENTS

| | | |
|---|---|---|
| 4,011,872 | 3/1977 | Komiya . |
| 4,121,592 | 10/1978 | Whalley . |
| 4,154,246 | 5/1979 | LeVeen . |
| 4,237,898 | 12/1980 | Whalley . |
| 4,280,503 | 7/1981 | Ackerman . |
| 4,311,154 | 1/1982 | Sterzer et al. . |
| 4,411,266 | 10/1983 | Cosman . |
| 4,423,727 | 1/1984 | Widran et al. . |
| 4,448,198 | 5/1984 | Turner . |
| 4,503,855 | 3/1985 | Maslanka . |
| 4,565,200 | 1/1986 | Cosman . |
| 4,601,296 | 7/1986 | Yerushalmi . |
| 4,658,836 | 4/1987 | Turner . |
| 4,665,906 | 5/1987 | Jervis . |
| 4,676,258 | 6/1987 | Inokuchi et al. . |
| 4,763,671 | 8/1988 | Goffinet . |
| 4,805,616 | 2/1989 | Pao . |
| 4,823,791 | 4/1989 | D'Amelio et al. . |
| 4,896,671 | 1/1990 | Cunningham et al. . |
| 4,907,589 | 3/1990 | Cosman . |
| 4,917,082 | 4/1990 | Grossi et al. . |
| 4,920,978 | 5/1990 | Colvin . |
| 4,950,267 | 8/1990 | Ishihara et al. . |
| 4,955,377 | 9/1990 | Lennox et al. . |
| 4,966,597 | 10/1990 | Cosman . |
| 4,979,948 | 12/1990 | Geddes et al. . |
| 5,007,908 | 4/1991 | Rydell . |
| 5,057,107 | 10/1991 | Parins et al. . |
| 5,078,716 | 1/1992 | Doll . |
| 5,083,565 | 1/1992 | Parins . |
| 5,084,044 | 1/1992 | Quint . |
| 5,098,431 | 3/1992 | Rydell . |
| 5,151,100 | 9/1992 | Abele et al. . |
| 5,159,925 | 11/1992 | Neuwirth et al. . |
| 5,186,181 | 2/1993 | Franconi et al. . |
| 5,191,883 | 3/1993 | Lennox et al. . |
| 5,192,280 | 3/1993 | Parins . |
| 5,197,963 | 3/1993 | Parins . |
| 5,220,927 | 6/1993 | Astrahan et al. . |
| 5,246,438 | 9/1993 | Langberg . |
| 5,249,585 | 10/1993 | Turner et al. . |
| 5,273,524 | 12/1993 | Fox et al. . |
| 5,282,799 | 2/1994 | Rydell . |
| 5,290,286 | 3/1994 | Parins . |
| 5,295,955 | 3/1994 | Rosen et al. . |
| 5,300,068 | 4/1994 | Rosar et al. . |
| 5,301,687 | 4/1994 | Wong et al. . |
| 5,304,214 | 4/1994 | DeFord et al. . |
| 5,318,563 | 6/1994 | Malis et al. . |
| 5,330,518 | 7/1994 | Neilson et al. . |
| 5,334,193 | 8/1994 | Nardella . |
| 5,341,807 | 8/1994 | Nardella . |
| 5,342,357 | 8/1994 | Nardella . |
| 5,364,392 | 11/1994 | Warner et al. . |
| 5,368,591 | 11/1994 | Lennox et al. . |
| 5,370,675 | 12/1994 | Edwards et al. . |
| 5,383,876 | 1/1995 | Nardella . |
| 5,383,917 | 1/1995 | Desai et al. . |
| 5,385,544 | 1/1995 | Edwards et al. . |
| 5,401,274 | 3/1995 | Kusunoki . |
| 5,403,311 | 4/1995 | Abele et al. . |
| 5,409,006 | 4/1995 | Buchholtz et al. . |
| 5,409,453 | 4/1995 | Lundquist et al. . |
| 5,413,588 | 5/1995 | Rudie et al. . |
| 5,421,819 | 6/1995 | Edwards et al. . |
| 5,423,808 | 6/1995 | Edwards et al. . |
| 5,431,649 | 7/1995 | Mulier et al. . |
| 5,435,805 | 7/1995 | Edwards et al. . |
| 5,437,662 | 8/1995 | Nardella . |
| 5,441,498 | 8/1995 | Perkins . |
| 5,454,782 | 10/1995 | Perkins . |
| 5,458,597 | 10/1995 | Edwards et al. . |
| 5,464,437 | 11/1995 | Reid et al. . |
| 5,464,445 | 11/1995 | Rudie et al. . |
| 5,470,308 | 11/1995 | Edwards et al. . |
| 5,470,309 | 11/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,507,743 | 4/1996 | Edwards et al. . |
| 5,509,929 | 4/1996 | Hascoet et al. . |
| 5,514,130 | 5/1996 | Baker . |
| 5,531,676 | 7/1996 | Edwards et al. . |
| 5,531,677 | 7/1996 | Lundquist et al. . |
| 5,536,240 | 7/1996 | Edwards et al. . |
| 5,540,655 | 7/1996 | Edwards et al. . |
| 5,540,681 | 7/1996 | Strul et al. . |
| 5,542,915 | 8/1996 | Edwards et al. . |
| 5,542,916 | 8/1996 | Hirsch et al. . |
| 5,545,161 | 8/1996 | Imran . |
| 5,599,294 | 2/1997 | Edwards et al. . |
| 5,599,345 | 2/1997 | Edwards et al. . |
| 5,599,346 | 2/1997 | Edwards et al. . |
| 5,993,447 | 11/1999 | Blewett et al. ............................ 606/50 |
| 5,995,875 | 11/1999 | Blewett et al. ............................ 607/98 |

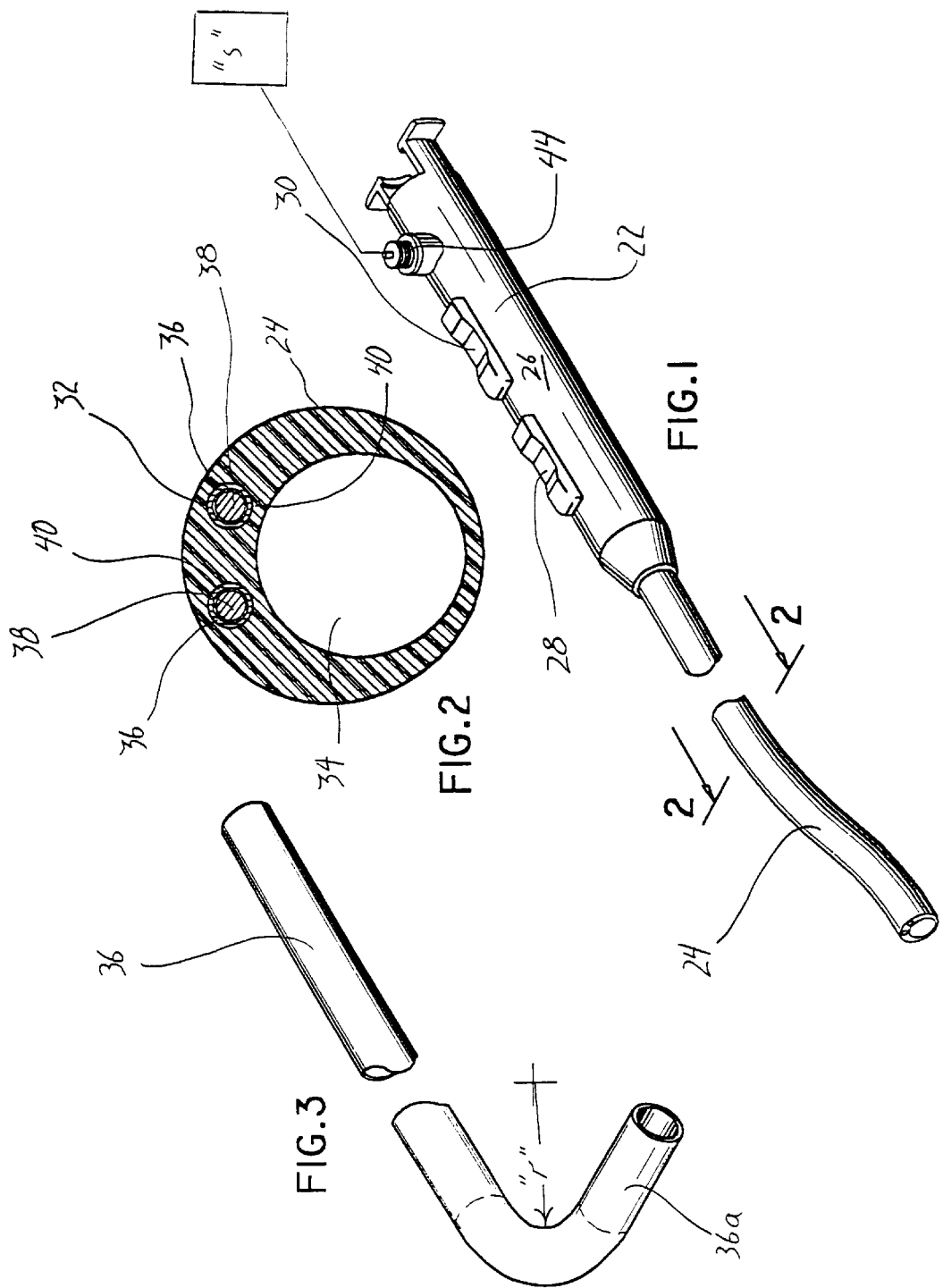

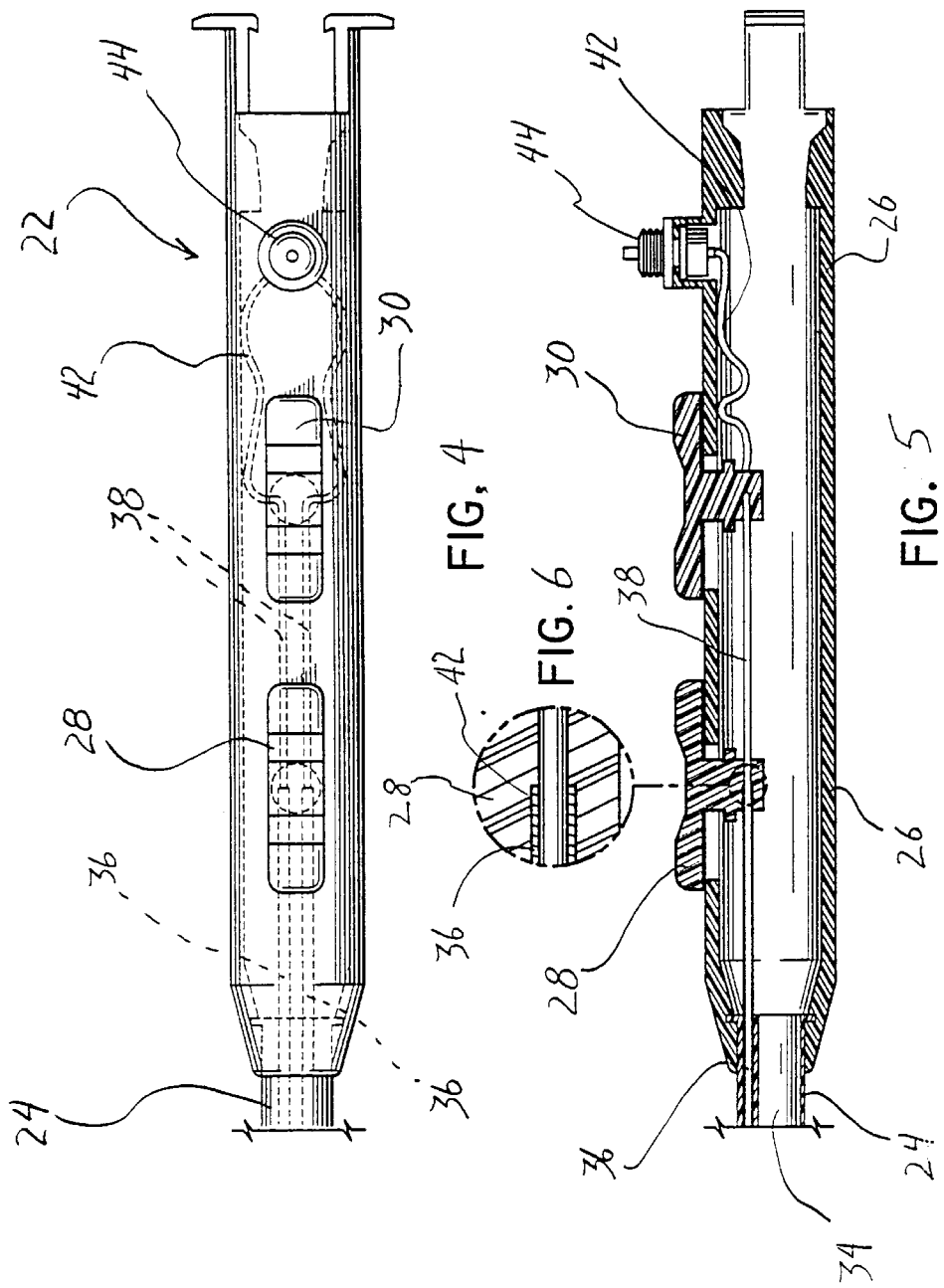

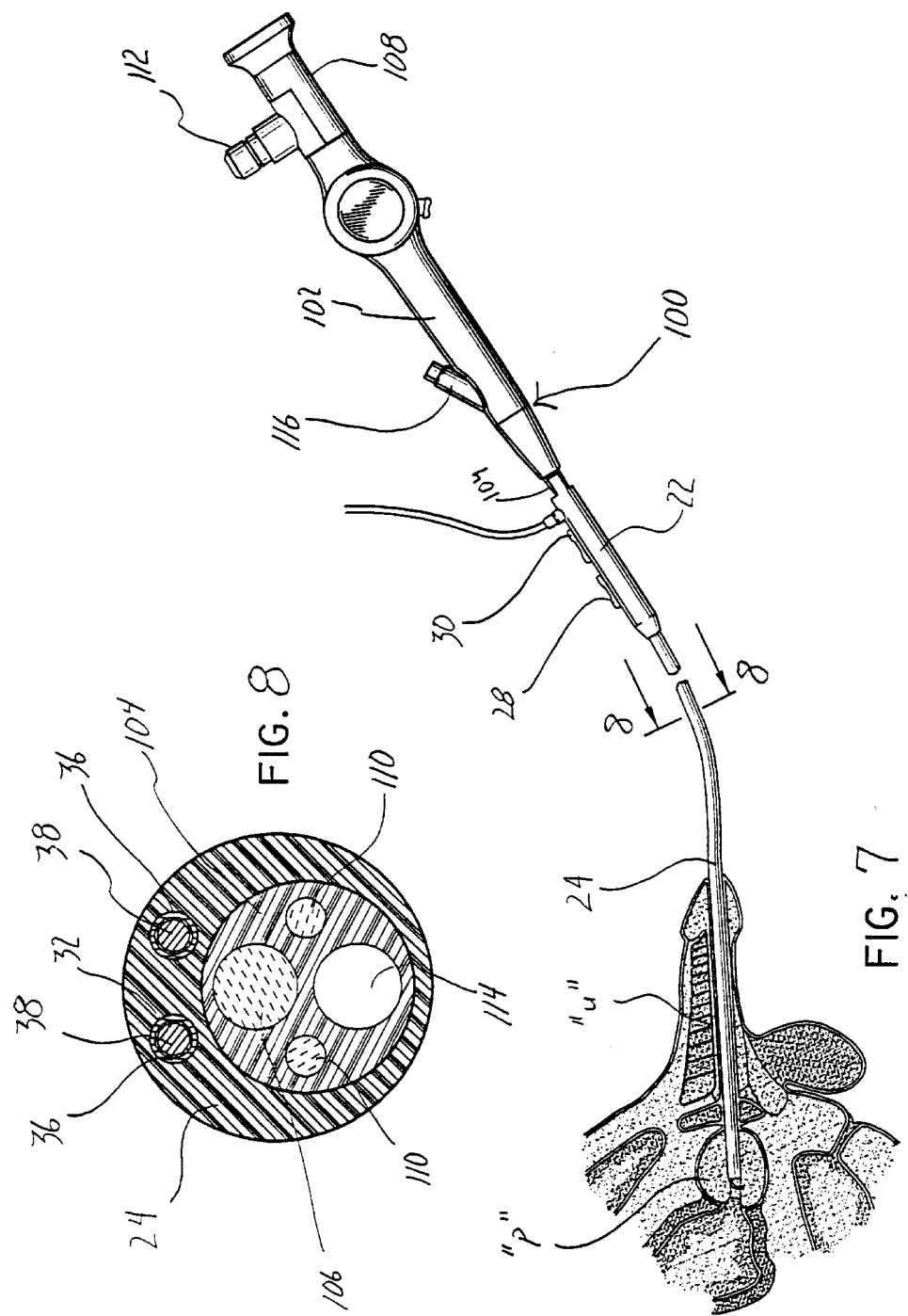

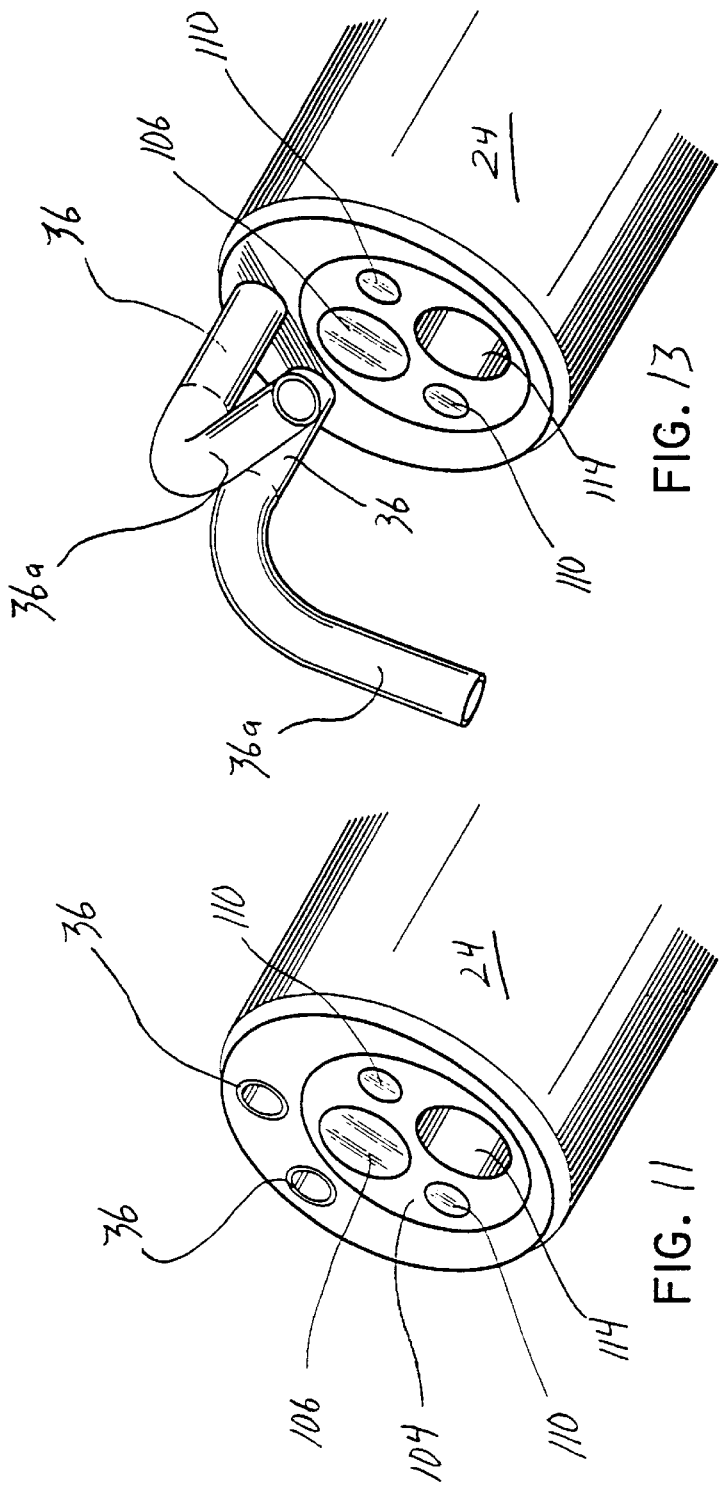
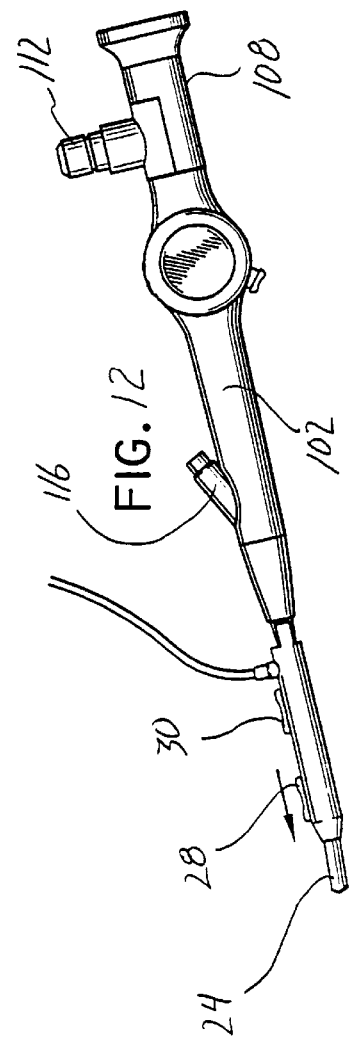
FIG. 13
FIG. 11
FIG. 12

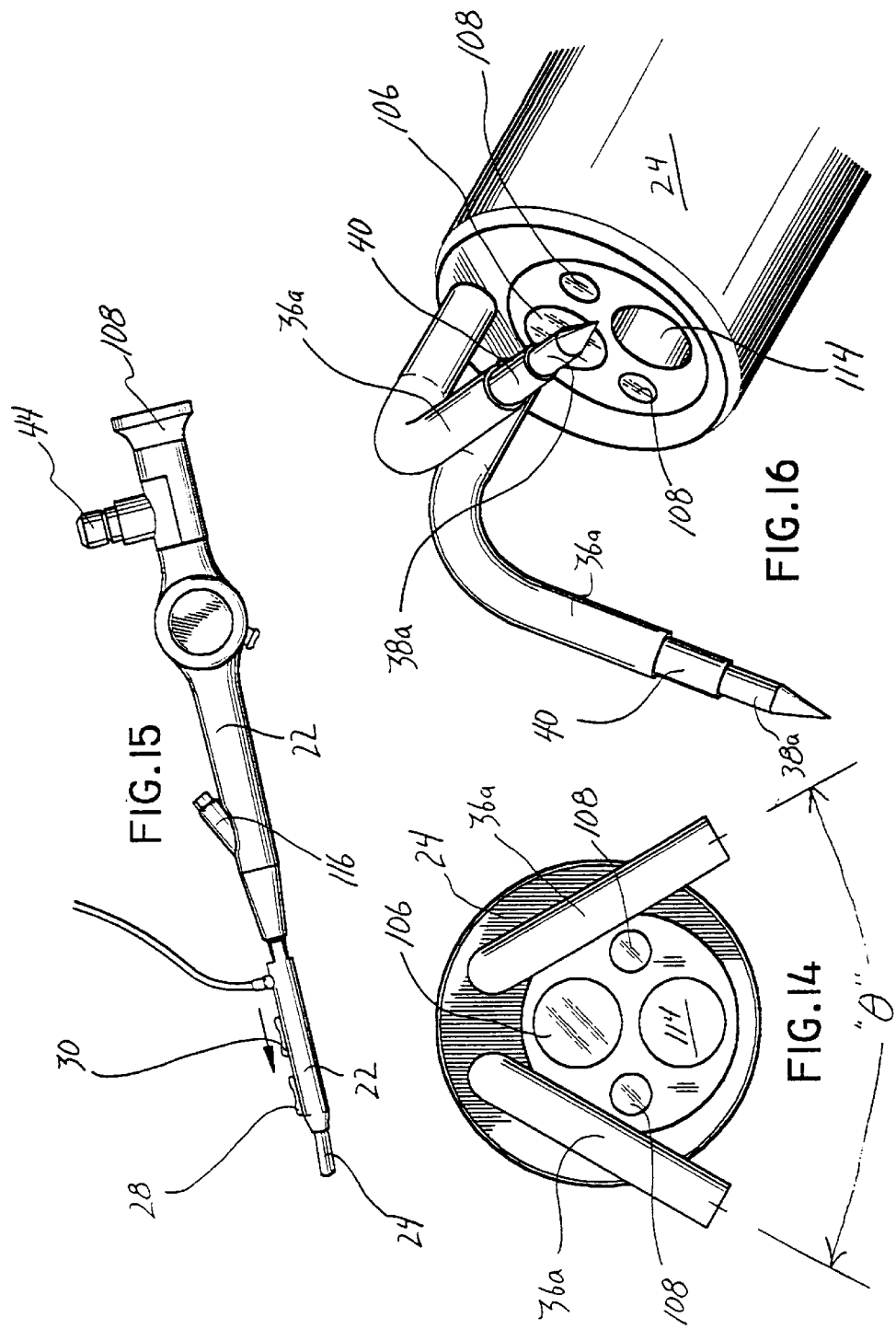

APPARATUS FOR THERMAL TREATMENT OF TISSUE

BACKGROUND

1. Technical Field

The present disclosure relates generally to a method and apparatus for thermal treatment of tissue and, more particularly, to a method and apparatus for the hyperthermic treatment of prostatic tissue.

2. Background of the Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, retrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary relief and requiring a subsequent repeat of the procedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

Transurethral microwave therapy (TUMT) and high intensity focused ultrasound (HIFU) have also been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applicators of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent form of treatment for BPH involves thermally treating prostatic tissue with radio frequency electromagnetic energy. For example, one current technique, known as transurethral needle ablation (TUNA™), involves the transurethral application of a medical instrument having a built-in RF needle electrode system. The TUNA™ instrument is inserted into the urethra and advanced to a position adjacent the prostate. Thereafter, the RF needles are advanced to penetrate the urethral wall and access the prostatic tissue. The RF system is activated whereby a RF current is transmitted through each electrode to pass through the tissue to a grounding pad thereby forming a necrotic lesion which is eventually absorbed by the body. Apparatuses and methods for treating BPH via the TUNA™ technique are disclosed in U.S. Pat. Nos.: 5,366,490; 5,370,675; 5,385,544; 5,409,453; 5,421,819; 5,435,805; 5,470,308; 5,470,309; 5,484,400; and 5,486,161.

SUMMARY

Accordingly, the present disclosure is directed to an apparatus for the radio-frequency (RF) thermal treatment of tissue, particularly, prostatic tissue and is intended for use in conjunction with an endoscope. In a preferred embodiment, the apparatus includes an elongated member having at least one passageway extending at least partially along its length, a delivery tube disposed within the passageway and having a memory portion comprised of a shape memory material, and being moveable within the passageway to extend the memory portion from the elongate member to permit the memory portion to assume a normal unstressed curved configuration, an electromagnetic probe disposed within the delivery tube and moveable within the delivery tube to extend a probe end portion beyond the delivery tube and within tissue. The electromagnetic probe has sufficient flexibility to follow the curved path defined by the memory portion of the delivery tube. The elongate member of the apparatus may further include a channel dimensioned to receive an endoscope. Proximally positioned actuators permit selective movement of the delivery tube and electromagnetic probe.

The present disclosure is also directed to a combination of a thermal treatment apparatus and an endoscope which is positioned within a bore of the apparatus. A method for thermally treating tissue is also disclosed.

BRIEF DESCRIPTION OF THE DRAWINGS

Preferred embodiment(s) of the present disclosure are described herein with reference to the drawings wherein:

FIG. 1 is a perspective view of the apparatus for thermal treatment of tissue in accordance with the principles of the present disclosure illustrating the handle and the elongate housing extending from the handle;

FIG. 2 is a cross-sectional view taken along the lines 2—2 of FIG. 1 illustrating the elongate housing with an axial bore for reception of an endoscope, electrode delivery tubes extending through the housing and the electrodes disposed within the delivery tubes;

FIG. 3 is a perspective view of one of the delivery tubes in a normal unstressed curved configuration;

FIG. 4 is a top plan view of the handle of the apparatus illustrating the tube actuator and the electrode actuator;

FIG. 5 is a side cross-sectional view of the handle;

FIG. 6 is an isolated view illustrating connection of the delivery tubes to the tube actuator;

FIG. 7 is a view illustrating insertion of the apparatus with mounted endoscope within the urethral passage of the patient;

FIG. 8 is a cross-sectional view taken along the lines 8—8 of FIG. 7 illustrating the endoscope inserted within the axial bore of the apparatus;

FIG. 11 is a perspective view of the distal end portion of the apparatus illustrating the electrode delivery tubes in their non-deployed positions;

FIG. 12 is a view illustrating distal movement of the tube actuator to deploy the distal end portion of the electrode delivery tubes;

FIG. 13 is a view similar to the view of FIG. 11 illustrating deployment of the electrode delivery tubes;

FIG. 14 is an axial view of the apparatus further depicting the deployment of the delivery tubes;

FIG. 15 is a view similar to the view of FIG. 12 illustrating distal movement of the electrode actuator to advance the electrodes through the electrode delivery tubes and within the patient's prostatic tissue;

FIG. 16 is a view similar to the view of FIG. 13 illustrating the electrodes in the advanced position.

DETAILED DESCRIPTION OF PREFERRED EMBODIMENTS

Figure 9:
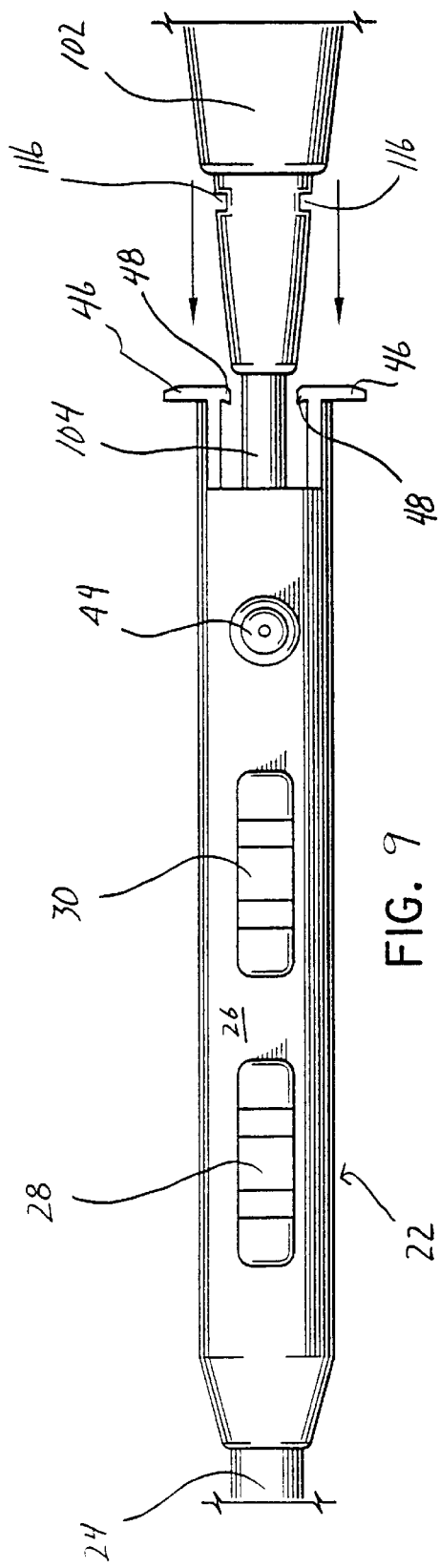
FIGS. 9–10 are side elevational views of the handle illustrating a preferred mechanism for mounting the endoscope to the handle.

The apparatus of the present disclosure is intended to deliver electromagnetic energy to tissue for thermal treatment of the tissue including tissue ablation, tissue vaporization and/or tissue coagulation. The apparatus has particular application in the treatment of benign prostate hyperplasia (BPH) with electromagnetic radio frequency (RF) energy, however, it is to be appreciated that the apparatus is not limited to such application. For example, the apparatus may be used in other surgical procedures such as cardiac ablation, cancer treatment, etc. . . . Moreover, the apparatus may be used in any minimally invasive procedure where thermal treatment of tissue is desired and access to the tissue is limited.

The apparatus which is preferably disposable, is adapted to be used in conjunction with a conventional endoscope such as a cystoscope, fiber scope, laparoscope, urethroscope, etc. . . . and has a bore configured for receiving the scope. The apparatus can also be designed of further reduced diameter to receive a specially designed endoscope or a plurality of optical fibers.

Referring now to FIGS. 1–2, apparatus 20 includes handle 22 and elongate member 24 connected to the handle 22 and extending distally therefrom. Handle 22 includes frame 26 which is preferably fabricated from a suitable rigid polymeric material or, in the alternative, from stainless steel or an aluminum alloy. Frame 26 is advantageously dimensioned to be grasped by the hands of the surgeon. Handle 22 further includes a first or delivery tube actuator 28 and a second or electrode actuator 30 which are each mounted for movement relative to the frame 26 to operate the apparatus.

Elongate housing 24 is preferably fabricated from a flexible elastomeric material such as silicone. This facilitates passage through the urethra and decreases patient discomfort. However, it is envisioned that alternatively elongate housing 24 may be rigid if, for example, it is intended to be used with a rigid scope. Elongate member 24 has two longitudinal passageways 32 extending therethrough and an enlarged channel or axial bore 34 eccentrically arranged relative to the central axis "a" of the housing 24. Channel 34 is configured for reception of an endoscope. Elongate member 24 is advantageously dimensioned for insertion into the urethral passage of the patient and preferably ranges from about 20 to about 50 millimeters (mm) in length, and, preferably about 24 mm, and preferably, about 7 to about 10 millimeters in diameter, preferably about 7.7 mm.

Referring now to FIGS. 2–3, an electrode delivery tube 36 is disposed within each longitudinal passageway 32 of elongate member 24 and each is adapted for reciprocal longitudinal movement within their respective passageways 32. Delivery tubes 36 accommodate electromagnetic probes (electrodes) 38 therein and serve in guiding the electrodes at desired orientations within the tissue. Delivery tubes 36 are preferably fabricated from a shape memory metal such as Nitinol. In the normal, i.e., unstressed condition of delivery tubes 36, the distal end portions 36a of the delivery tubes each assume the arcuate configuration depicted in FIG. 3, i.e., the distal end portions have memory to defined the arcuate orientation as shown thereby providing arcuate paths for the electrodes to follow to penetrate and ablate tissue. The particular orientation of memory portions 36a can be varied depending on the objectives of the surgical procedures. The distal end portions 36a of delivery tubes 36 readily adapt a linear configuration when confined within their respective passageways 32 of elongate member 24 as will be discussed. In a preferred embodiment (in BPH application), memory portions 36a of delivery tubes define a radius of curvature "r" (FIG. 3) ranging between about 250 to about 0.400 inches, more preferably, about 0.312 inches. Other radii of curvature are envisioned as well.

With particular reference to FIG. 2, electromagnetic probes 38 disposed within delivery tubes 36 include bipolar electrodes formed of a thin solid wire capable of carrying an electromagnetic radiofrequency (RF) current. The electrodes 38 are relatively flexible to follow along the path defined by delivery tubes 36, but, sufficient in rigidity to be advanced into tissue. The electrodes are preferably made of Nitinol so they can return to their normally straight configuration after being bent by the delivery tubes. The electrodes each have a pointed tip to facilitate penetration through the tissue. Each electrode has an insulating layer, designated by reference numeral 40, which extends along a major portion of its length to prevent damage to non-targeted body tissue. (see also FIG. 16). Each electrode is electrically isolated from its delivery tube. Insulating layer 40 terminates to expose the distal penetrating portions of the electrodes 38, thus, permitting the transmission of electromagnetic RF current to the targeted body tissue.

Referring now to FIGS. 4–6, each delivery tube 36 is connected to tube actuator 28 of handle 22. In one preferred arrangement, tube actuator 28 includes a recess 42 which accommodates the proximal ends of delivery tubes 36 in interfitting relation as depicted in FIG. 6. Other mounting arrangements for connecting tube actuator 28 and delivery tubes 36 are envisioned as well such as the use of adhesives, screws, or the like.

Longitudinal movement of tube actuator 28 causes corresponding longitudinal movement of delivery tubes 36 within passageways 32 of elongate member 24. That is, tube actuator 28 is moveable (slideable) to cause reciprocal movement of delivery tubes 36 between a first retracted position where the distal end or memory portions 36a of delivery tubes 36 are contained within their respective passageways 32 of elongate member 24 and a second advanced position where the distal end portions 36a extend beyond the distal end of the elongate member 24 and assume their angularly oriented positions.

Electrode actuator 30 is operatively connected to electromagnetic probes 38 disposed within delivery tubes 36. In a preferred embodiment the probes are connected to the actuator 30 by a crimped ferrule. Any conventional means appreciated by one skilled in the art for connecting electrode actuator 30 to electromagnetic probes 38 may be utilized.

Electrode actuator 30 is moveable to cause corresponding motion of electromagnetic probes 38 within their respective delivery tubes 36 to extend the penetrating end portions of the probes 38 beyond the tubes for deployment into tissue. As seen in FIGS. 4 and 6, a pair of conductive wires 42 are provided to connect electromagnetic probes 38 to coupling 44 mounted to handle 22. Coupling 44 is connectable to an external radio frequency energy source "s" as schematically depicted in FIG. 1.

Referring now to FIG. 7, apparatus 20 is shown with a conventional reusable endoscope 100 positioned therein for thermal treatment of prostate "p" to alleviate the symptoms of BPH. One conventional cystoscope 100 with which the apparatus of the present disclosure can be utilized is the ACN Flexible CystoNephroscope manufactured by Circon ACMI. Cystoscope 100 includes handle 102 and a flexible elongated portion 104 connected to the handle 102 and extending distally therefrom. Elongated portion 104 is positioned within the bore 34 of apparatus as depicted in FIG. 8. Cystoscope 100 incorporates an optical system to permit viewing of the tissue to be treated. The optical system preferably consists of flexible fiber optic bundles (identified by reference numeral 106) which are accommodated within a longitudinal bore extending through the elongated portion 104 of the scope 100. Optical systems incorporating optical lens arrangements or electronic optical components, e.g., CCD's, are envisioned as well. The fiber optic bundles 106 extend to eyepiece 108 where the surgeon can view the image transmitted by the optical system.

Cystoscope 100 also includes an illumination system which provides illuminating light to the targeted tissue area. The illumination system includes a plurality of optical fibers 110 which are accommodated within a plurality of longitudinal channels (two are shown) of elongated portion 104 and extend within handle 102 where they terminate at illumination coupler 112. Illumination coupler 112 is connectable to a conventional light source as is known in the art. Cystoscope 100 may further includes a working channel 114 extending through flexible elongated portion 104 and terminating at channel port 116 of handle 102. Working channel 114 is adapted to receive various surgical instrumentation to permit the performance of surgical procedures at the distal end of the cystoscope 100. Working channel 114 may also serve as an irrigation conduit to receive irrigation fluids for dispensing at the distal end of the scope 100 to cool tissue adjacent the treatment area, e.g., the urethra lining.

Figure 10:
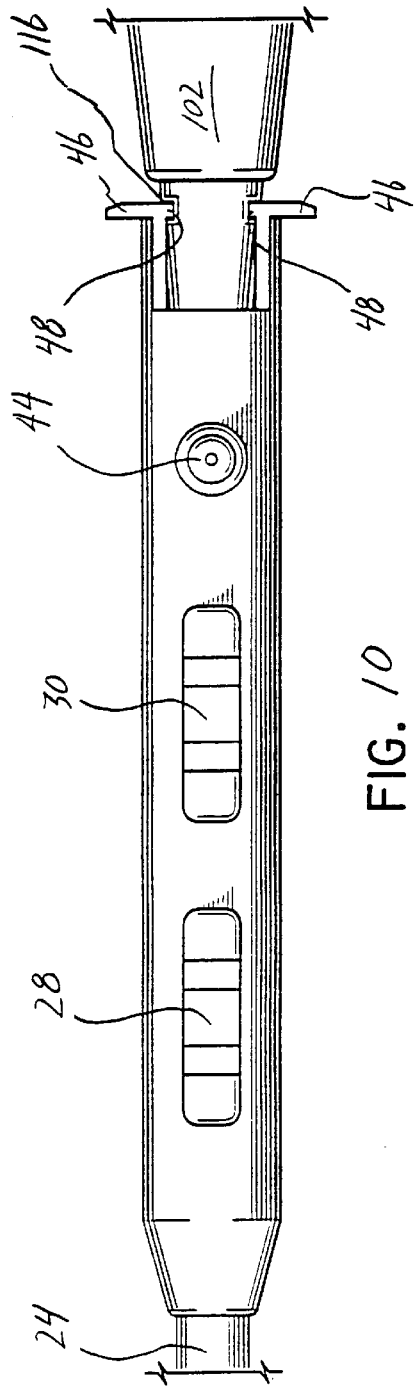

As depicted in FIGS. 9–10, apparatus 20 is releasably mountable to endoscope 100 through a tab and recess arrangement. In particular, handle 22 of apparatus 20 defines two diametrically opposed resilient tab members 46. Tab members 46 each have radially inwardly extending detents 48. Detents 48 are received within correspondingly dimensioned grooves 116 defined at the distal end of handle 102 of scope 100 to detachably mount the apparatus to the scope. In particular, tab members 46 flex outwardly upon insertion of cystoscope 100 within apparatus 20 to permit detents 48 to lockingly engage grooves 116 of scope 100 as depicted in FIG. 10. Other means for detachably mounting apparatus 20 to scope 100 are envisioned as well such as the use of a bayonet coupling or the like.

Operation

The use of apparatus 20 with cystoscope 100 in conjunction with the thermal treatment of prostatic tissue will now be discussed. With reference again to FIG. 7, apparatus 20 is inserted through urethral passage "u" of the patient and advanced within the passage until the distal end of the apparatus is adjacent prostate gland "p". Thereafter, endoscopic portion 104 of cystoscope 100 is inserted into bore 34 of apparatus 20 and advanced therein to engage the locking tab and recess arrangement thereby mounting the endoscope 100 to the apparatus 20 in the manner discussed above and depicted in FIG. 10. As an alternative method of insertion, cystoscope 100 may be positioned within apparatus 20 prior to insertion of the apparatus 20 within the urethral passage "u" and the entire assembly may be then advanced within the urethral passage "u".

With reference now to FIG. 11, delivery tubes 36 are shown in their retracted position. In such position, the distal end portions 36a of delivery tubes 36 are constrained within passageways 32 of elongated member 24 thereby assuming a general linear configuration within the passageways 32. Thereafter, tube actuator 28 is distally advanced as depicted in FIG. 12 to move delivery tubes 36 from their retracted positions of FIG. 11 to their extended positions of FIG. 13. Upon exiting passageways 32 of apparatus 20, the distal ends or memory portions 36a of delivery tubes 36 are no longer constrained by elongated member 24, and, thus, are free to assume their normal unstressed curved configurations depicted in FIGS. 13 and 14. By exiting through the distal end face of the apparatus 20, the deployment of delivery tubes 36 can be monitored with the optical system 106 of cystoscope 100. In the extended position of delivery tubes 36, the distal end portions 36a may slightly extend beyond the outer circumference of apparatus, 20, but, however, do not penetrate the urethral lining "u". In the deployed position, distal end portions 36a of delivery tubes 36 define an angle of divergence "T" (FIG. 14) preferably ranging from about 30·–90·, more preferably, about 60·.

Referring now to FIGS. 15–16, with distal end portions 36a in their extended positions, attention is directed to deploying the electromagnet probes 38. Electrode actuator 30 is selectively distally advanced to advance electromagnetic probes 38 from delivery tubes 36 as depicted in FIG. 16. During advancing movement, the penetrating end portions 38a of electrodes 38 flex or bend to conform to the curved configuration of distal end portions 36a of the delivery tubes 36 to pierce the urethral wall "u" and enter the prosthetic tissue "p".

The system is then energized to thermally treat (e.g., ablate, vaporize or cauterize) the desired prosthetic tissue with RF energy. (Microwave or other form of electromagnetic energy can alternatively be utilized.) As a result of this treatment, the prosthetic tissue necroses and dies, thus, relieving pressure off the urethral wall "u" and alleviating the symptoms of BPH. During treatment, the depth of penetration of penetrating end portions 38a of electromagnetic probes 38 may be selectively adjusted by movement of electrode actuator 30 to permit specific regions of the prosthetic tissue "p" to be targeted for thermal treatment thereby providing heating pattern flexibility and control. During treatment, insulating layer 40 of electromagnetic probes 38 contact the urethral wall "u" to prevent damage to the wall.

Upon completion of the procedure, the system is de-energized and the cystoscope 100 and apparatus 20 are removed from the urethral passage "u".

Figure 17:
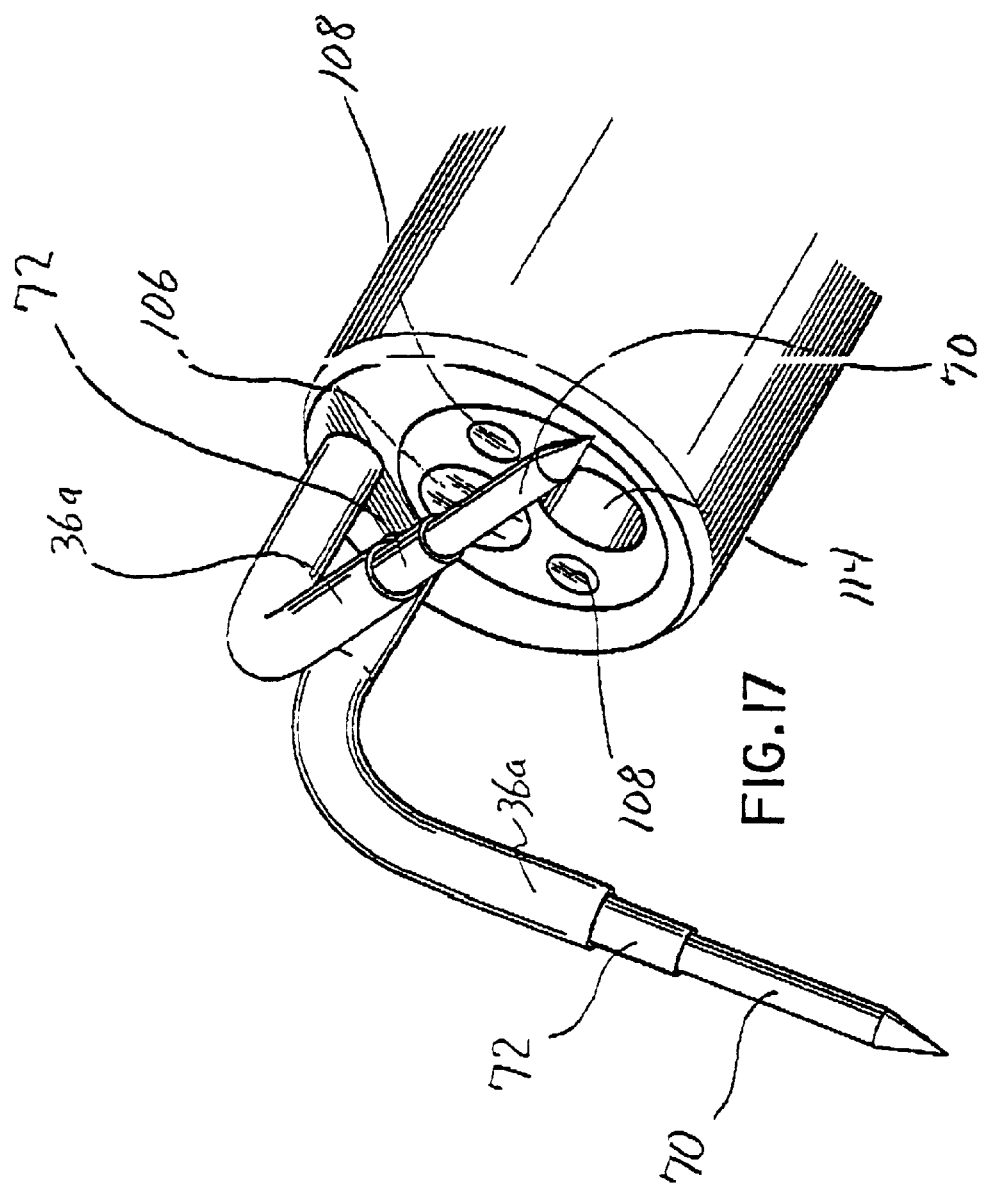
FIG. 17 is a perspective view of the distal end of an alternate embodiment of thermal treatment apparatus of FIG. 1 where a greater portion of the electrode is exposed to provide a greater thermal treatment capacity.

FIG. 17 depicts the distal end portion of an alternate embodiment of the thermal treatment apparatus of FIG. 1. This embodiment is substantially similar to the prior embodiment. However, in accordance with this embodiment, a greater portion of each electrode 70 is exposed (i.e., uninsulated by insulating layer 72) to provide a greater range or area of thermal treatment. (Compare with FIG. 16). It is to be appreciated that the lengths of the exposed electrode portions may be varied to achieve desired thermal treatment objectives.

Although two delivery tubes and two electrodes are shown and described above, it is contemplated that one delivery tube or electrode could be provided. Also, three or more delivery tubes and electrodes could be utilized. Both bipolar and monopolar applications are also contemplated.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An apparatus for thermal treatment of tissue comprising an elongate member including at least one passageway extending at least partially along its length, a delivery tube disposed within the passageway and having a memory portion comprised of a shape memory material, the delivery tube moveable within the passageway to extend the memory portion from the elongate member to permit the memory portion to assume a normal unstressed curved configuration, an electromagnetic probe disposed within and electrically isolated from the delivery tube and moveable within the delivery tube to extend a probe end portion beyond the delivery tube and within tissue, the electromagnetic probe having sufficient flexibility to follow the curved configuration of the memory portion of the delivery tube, the electromagnetic probe including an electrode and an insulating layer coaxially mounted about the electrode.

2. The apparatus according to claim 1 including a proximally positioned tube actuator operatively connected to the delivery tube, the tube actuator moveable to move the delivery tube to extend the memory portion from the elongate member.

3. The apparatus according to claim 2 including a proximally positioned probe actuator operatively connected to the electromagnetic probe, the probe actuator moveable to move the electromagnetic probe to extend the probe end portion beyond the delivery tube.

4. The apparatus according to claim 3 further including:
first and second delivery tubes; and
first and second electromagnetic probes being disposed with respective first and second delivery tubes.

5. The apparatus according to claim 3 wherein the shape memory material comprises a memory metal.

6. The apparatus according to claim 1 wherein the elongate member includes a channel at least partially extending therealong, the channel dimensioned to receive surgical instrumentation.

7. The apparatus according to claim 1 wherein the elongate member includes at least two passageways, each passageway having a delivery tube therein, an electromagnetic probe being disposed within each delivery tube.

8. The apparatus according to claim 1, wherein the passageway terminates in a distal opening defined in a distal end face of the elongate member.

9. The apparatus according to claim 8, wherein the elongate member has a bore formed therein dimensioned to receive an endoscope such that advancement of the electromagnetic probe through the passageway and out the distal opening can be visualized when the endoscope is mounted within the bore.

10. The apparatus according to claim 1 wherein the probe is a RF electrode.

11. The apparatus according to claim 10 including an RF energy source operatively connected to the electromagnetic probe.

12. The apparatus according to claim 1 wherein the elongate member is flexible.

13. A system for thermal treatment of tissue which comprises:
a thermal treatment apparatus including:
a handle portion;
an elongate member extending distally from the handle portion, the elongate member including a bore extending at least partially therethrough dimensioned for reception of an endoscope;
at least one delivery tube supported within the elongate member and mounted for movement therein, the delivery tube having a memory portion comprised of a shape memory material and defining a normal unstressed curved orientation;
an electromagnetic probe disposed within and electrically isolated from the delivery tube and mounted for reciprocal movement therein, the electromagnetic probe including an electrode and an insulating layer coaxially arranged about the electrode;
a tube actuator mounted to the handle portion and operatively connected to the delivery tube, the tube actuator moveable to extend the memory portion of the delivery tube from the elongate member to permit the delivery tube to assume its normal unstressed curved orientation; and
a probe actuator mounted to the handle portion and operatively connected to the probe, the probe actuator moveable to move the probe to thereby extend the probe end portion beyond the delivery tube; and an endoscope at least partially positioned within the bore of the thermal treatment apparatus, the endoscope including:
a frame; and
an endoscopic portion extending from the frame, the endoscopic portion dimensioned for insertion into the bore of the elongate member of the thermal treatment apparatus, the endoscope enabling visualization of the delivery tube as the delivery tube exits the elongate member and enabling visualization of the probe as the probe extends beyond the delivery tube.

14. The system of claim 13 including a pair of delivery tubes disposed within respective longitudinal passageways defined within the elongate member.

15. The system of claim 14 wherein the longitudinal passageways of the elongate member extend through a distal end face of the elongate member.

16. The apparatus according to claim 13 including a radio-frequency energy generator connected to the electromagnetic probes.

17. The apparatus according to claim 16 wherein the shape of memory material comprises a memory metal.

* * * * *